(12) United States Patent
Fox et al.

(10) Patent No.: US 9,696,257 B2
(45) Date of Patent: Jul. 4, 2017

(54) AUTOMATED AND ACCURATE DROP DELAY FOR FLOW CYTOMETRY

(71) Applicant: Bio-Rad Laboratories, Inc., Hercules, CA (US)

(72) Inventors: Daniel N. Fox, Bellvue, CO (US); Susan Hunter, Fort Collins, CO (US); Nathan Michael Gaskill-Fox, Fort Collins, CO (US); Kevin P. Raley, Windsor, CO (US); Richard A. Miles, Fort Collins, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1049 days.

(21) Appl. No.: 13/912,602

(22) Filed: Jun. 7, 2013

(65) Prior Publication Data
US 2013/0337575 A1  Dec. 19, 2013

Related U.S. Application Data

(60) Provisional application No. 61/656,934, filed on Jun. 7, 2012.

(51) Int. Cl.
| | |
|---|---|
| *G01N 33/49* | (2006.01) |
| *G01N 33/86* | (2006.01) |
| *G01N 15/14* | (2006.01) |
| *G01N 21/64* | (2006.01) |
| *G01N 15/10* | (2006.01) |

(52) U.S. Cl.
CPC ......... *G01N 21/64* (2013.01); *G01N 15/1012* (2013.01); *G01N 15/1427* (2013.01); *G01N 15/1459* (2013.01); *G01N 2015/1006* (2013.01); *G01N 2015/1406* (2013.01); *G01N 2015/149* (2013.01)

(58) Field of Classification Search
CPC .... G01N 33/4905; G01N 33/86; G01N 33/49; G01N 33/483; G01N 33/48; G01N 33/50; G01N 33/582; G01N 33/58; G01N 21/6428; G01N 21/64; G01N 21/63; G01N 21/62
USPC ..................... 436/172, 164; 422/73, 68.1, 50
See application file for complete search history.

(56) References Cited

U.S. PATENT DOCUMENTS

| | | | |
|---|---|---|---|
| 3,981,019 A * | 9/1976 | Fujimoto | G01D 15/18 327/28 |
| 4,009,435 A | 2/1977 | Hogg | |

(Continued)

FOREIGN PATENT DOCUMENTS

CN     101750272 A     6/2010

OTHER PUBLICATIONS

International Search Report and Written Opinion dated Oct. 31, 2013 for International Application No. PCT/US13/44692.

(Continued)

*Primary Examiner* — Christine T Mui
(74) *Attorney, Agent, or Firm* — Weaver Austin Villeneuve & Sampson LLP (57) ABSTRACT

Disclosed is an automated method and apparatus for automatically setting a drop delay period by detecting calibration particles in a waste stream. The drop delay is incremented over a series of drop delays and the number of calibration particles in the waste stream is detected for each drop delay. The drop delay is selected which has the least number of calibration particles in the waste stream.

8 Claims, 7 Drawing Sheets

(56) References Cited

U.S. PATENT DOCUMENTS

| | | | |
|---|---|---|---|
| 4,616,234 A * | 10/1986 | Wint | B41J 2/115 347/80 |
| 5,483,469 A | 1/1996 | Van den Engh | |
| 5,643,796 A | 7/1997 | Van den Engh | |
| 6,097,485 A | 8/2000 | Lievan | |
| 6,248,590 B1 * | 6/2001 | Malachowski | G01N 15/1404 209/127.4 |
| 6,372,506 B1 | 4/2002 | Norton | |
| 7,232,687 B2 * | 6/2007 | Lary | G01N 15/1404 209/127.4 |
| 2004/0086159 A1 | 5/2004 | Lary et al. | |
| 2005/0042760 A1 * | 2/2005 | Yount | G01N 15/1459 436/63 |
| 2005/0227362 A1 | 10/2005 | Lary et al. | |
| 2010/0177305 A1 | 7/2010 | Chen | |
| 2012/0044480 A1 | 2/2012 | Javadi et al. | |

OTHER PUBLICATIONS

International Preliminary Report on Patentability dated Dec. 9, 2014 for International Application No. PCT/US13/44692.
Chinese Office Action dated May 31, 2016 for CN Application No. 201380029935.6.
"Clinical testing of equipment and in-vitro diagnostic reagent", Personnel Department of National Food and Drug Administration, Oct. 31, 2010, 4 pp. [no translation—as noted on front page of reference].
Riddel, A., et al., "*Rmax*: A systematic approach to evaluate instrument sort performance using center stream catch," Methods 82, 2015, pp. 64-73.
EP Search Report in corresponding EP Application No. 13801005.3, issued Dec. 9, 2015.
Chinese Office Action dated Feb. 20, 2017 for CN Application No. 201380029935.6.

* cited by examiner

//AUTOMATED AND ACCURATE DROP DELAY FOR FLOW CYTOMETRY

CROSS-REFERENCE TO RELATED APPLICATION

This application is based upon and claims priority to U.S. provisional application Ser. No. 61/656,934, filed Jun. 7, 2012, entitled "Automated and Accurate Drop Delay for Flow Cytometry," which application is specifically incorporated herein by reference for all that it discloses and teaches.

BACKGROUND

Flow cytometers are useful devices for analyzing and sorting various types of particles in fluid streams. These cells and particles may be biological or physical samples that are collected for analysis and/or separation. The sample is mixed with a sheath fluid for transporting the particles through the flow cytometer. The particles may comprise biological cells, calibration beads, physical sample particles, or other particles of interest, which are collectively referred to herein as "particles." Sorting and analysis of these particles can provide valuable information to both researchers and clinicians. In addition, sorted particles can be used for various purposes to achieve a wide variety of desired results.

SUMMARY

An embodiment of the present invention may therefore comprise a method of automatically selecting a drop delay period in a flow cytometer comprising: operating the flow cytometer with calibration particles using a plurality of different drop delay periods; deflecting droplets that are charged using the plurality of different drop delay periods; collecting non-deflected droplets in a waste stream for each drop delay period of the plurality of drop delay periods; interrogating the waste stream to cause fluorescent emissions of the calibration particles in the waste stream for each drop delay period; sensing the fluorescent emissions from the calibration particles with a detector for each drop delay period; collecting data regarding a number of calibration particles sensed in the waste stream for each drop delay period; selecting a desired drop delay period from the plurality of different drop delay periods that has a substantially minimal number of the number of calibration particles sensed in the waste stream.

An embodiment of the present invention may further comprise a system for selecting a drop delay period using calibration particles in a flow cytometer comprising: a waste stream that is generated from droplets that are not deflected in the flow cytometer using a plurality of drop delay periods; a waste stream receiver that receives the waste stream; a waste stream interrogation optical source that interrogates the waste stream in the waste stream receiver for each drop delay period of the plurality of drop delay periods; a detector that senses fluorescent emissions from the calibration particles in the waste stream for each drop delay period; an analyzer that determines an amount of the calibration particles in the waste stream for the each drop delay period and selects a drop delay period based upon the amount of the calibration particles in the waste stream.

DETAILED DESCRIPTION OF THE EMBODIMENTS

Figure 1:
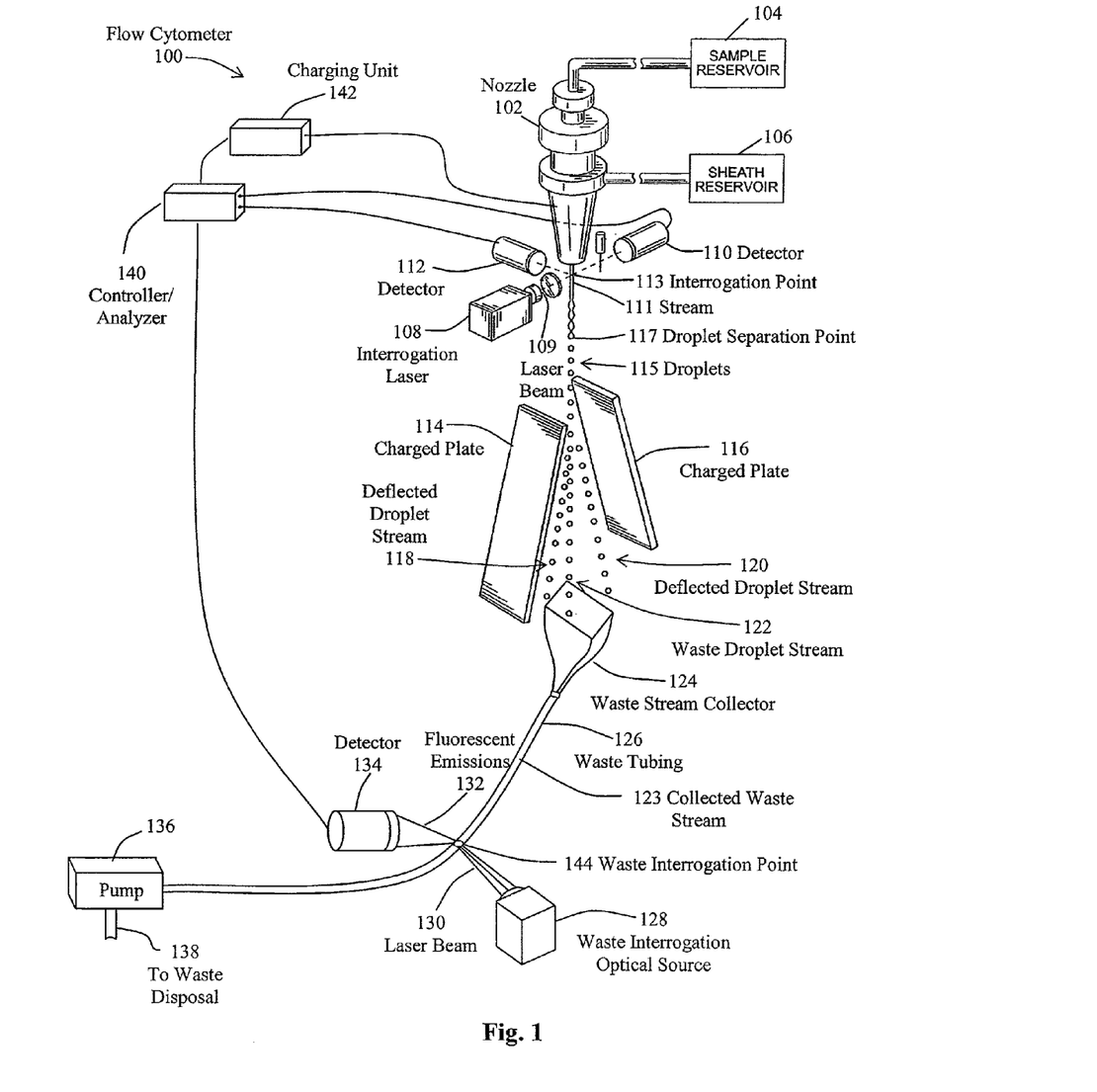
FIG. 1 is a schematic isometric view of an embodiment of the invention.

FIG. 1 is a schematic isometric view of an embodiment of the present invention. As illustrated in FIG. 1, a nozzle 102 receives a sample, which includes particles, e.g., biological cells, calibration beads or other particles (collectively referred to herein as "particles") from a sample reservoir 104. The particles are mixed with a sheath fluid from sheath reservoir 106 in the nozzle 102. This creates a stream 111 which comprises a liquid sheath that is formed around the particles from the sample reservoir 104 that helps to impart a substantially uniform velocity and flow of the particles in stream 111. The particles in the stream 111 intersect a laser beam 109 from the interrogation laser 108. The point at which the laser beam 109 intersects the stream 111 is referred to as interrogation point 113. As particles move through the interrogation point 113, the particles may cause the laser beam 109 to scatter. In addition, the laser beam may excite the particles, which have fluorescent properties, such as fluorescent markers, that adhere to or are contained within certain particles of interest. Alternatively, calibration beads that have fluorescent properties may be included in the stream 111. In this manner, the drop delay time (explained below) can be determined using calibration beads, rather than sample particles. In addition, the calibration beads may provide a more accurate way of setting the drop delay time because the fluorescent response of the calibration beads is strong.

The scattered light is normally detected by detector 110 while the fluorescent emissions are detected by detector 112. Detectors 110, 112 are normally photomultiplier tubes that can be quite expensive. Detectors 110, 112 can also comprise photodiodes or other light detecting devices, which receive light emitted at the interrogation point 113. Controller/analyzer 140 is connected to detectors 110, 112, which analyzes the data generated by detectors 110, 112 to generate a control signal to activate the charging unit 142 to sort cells based upon physical and fluorescent properties, as detected by detectors 110, 112. The process of sorting is explained in more detail below.

The embodiment of FIG. 1 illustrates an example of a method for electrostatically separating droplets 115 using charged plates 114, 116. The sheath fluid and sample that exit the nozzle 102 initially form a stream 111, which separates into individual droplets 115. To assist in causing the droplets to consistently form at a selected and consistent location along the stream 111, the stream 111 is vibrated, typically by a piezoelectric device (not shown). The droplets 115 form at a droplet separation point 117, which is a certain consistent distance along the stream 111, depending upon the velocity, viscosity and size of the stream 111, as well as the intensity and frequency of the piezoelectric vibrator. For each new nozzle 102, the distance between the interrogation point 113 and the droplet separation point 117 varies. The distance between the interrogation point 113 and the droplet separation point is referred to as the drop delay distance. The drop delay distance can be varied by varying the piezoelectric vibration. The time that it takes for a cell to move from the interrogation point 113 to the droplet separation point 117, i.e., the drop delay distance, is referred to as the drop delay time. Also, the sheath fluid from sheath reservoir 106 is electrically conductive, since it contains electrolytes, such as various salts.

The controller/analyzer 140 of FIG. 1 functions to generate a control signal that is applied to the charging unit 142 to charge the electrically conductive stream 111 with either a positive or negative charge. If a droplet is being formed that includes a particle of interest, a positive or negative charge is applied to stream 111, depending upon the type of particle, which is isolated into a droplet 115. Accordingly, when a particle of interest is detected by detectors 110, 112, the drop delay time between the travel of a cell between the interrogation point 113 and the droplet separation point 117 must be known very accurately so that the proper droplet is charged. If the proper droplet is charged, the droplet will be deflected either into deflected droplet stream 118 or deflected droplet stream 120, depending upon the charge of the droplet. If the droplet is uncharged, the droplet will fall directly downwardly in the waste droplet stream 122 and not be deflected into either deflected droplet stream 118, 120. In other words, when the stream 111 is charged by the charging unit 142 through the nozzle 102, just before the droplet 115 separates from the stream 111 at the droplet separation point 117, the charge on the stream 111 will be isolated in a droplet 115. The isolated charge in the droplet 115 will then cause the droplet to be deflected by charged plates 114, 116, so that the droplet is deflected into either deflected droplet stream 118 or deflected droplet stream 120, based upon the isolated charge of the droplet.

As can be readily appreciated, the travel time delay of particles from the interrogation point 113 to the droplet separation point 117 (droplet delay distance), which is referred to as the "drop delay time" or "drop delay period," is critical in the process of charging the proper droplet that contains the particles of interest. If a correct drop delay time is not used, a cell of interest may end up in the waste droplet stream, or in an incorrect deflected droplet stream 118, 120.

The deflected droplet streams 118, 120 are collected in deflected droplet stream reservoirs (not shown). The waste droplet stream 122 is collected in a waste stream collector 124. The waste stream collector 124 is connected to a waste tubing 126. The waste tubing 126, in one example, may comprise FEP tubing with an internal diameter of 0.5 mm and an external diameter of 1/16 inch. Pump 136 pumps the collected waste from the waste stream collector 124 through the waste tubing 126 to a waste disposal 138. To keep the collected waste stream from backing up in the waste tubing 126, pump 136 pumps the collected waste stream 123 at a rate that is slightly faster than the rate at which fluid enters the waste tubing 126. For example, in one embodiment, fluid enters the waste tubing 126 at approximately 8 mL/min and the waste pump 136 is operated at approximately 12 mL/min. Optical source 128 generates a beam 130 that interrogates the collected waste stream 123 in the waste tubing 126 at a wavelength of approximately 532 nm. The optical source may comprise a laser, an LED, or other optical source. The beam 130 is focused on a waste interrogation point 144 to interrogate the waste droplet stream collected in the waste tubing 126. The FEP material of the waste tubing 126 is substantially transparent to the beam 130 at 532 nm,
so that the laser beam 130 can interrogate the collected waste stream 123 in the waste tubing 126 at the waste interrogation point 144. In addition, the waste tubing 126 is substantially transmissive to the fluorescent emissions of calibration particles interrogated by the beam 130 at waste interrogation point 144. The fluorescent emissions 132 are gathered and focused on the detector 134, which detects the presence of fluorescent emissions of calibration particles in the collected waste stream 123 in the waste tubing 126.

When the detector 134 detects the presence of fluorescent emissions, as shown in FIG. 1, the detector 134 generates a signal that is applied to the controller/analyzer 140. Fluorescent emissions are created by calibration particles that have fluorescent markers, or are made with a fluorescent material, including calibration beads that are typically used for calibrating the drop delay. It should be noted that the drop delay can also be calculated with actual samples that have fluorescent markers, or by detecting scattered light from samples or calibration particles. Pump 136 draws the collected waste stream 123 through the waste tubing 126 at a substantially constant rate, which allows the detector 134 to detect calibration particles in the collected waste stream 123 at a substantially constant rate. Each time the detector 134 detects a fluorescent emission, an electrical signal is transmitted to the controller/analyzer 140. The controller/analyzer 140 collects and analyzes the data, as explained in more detail below. The existence of calibration particles in the collected waste stream 123 is an indication of whether the drop delay time is properly set in the flow cytometer 100. As explained below, data relating to the existence of calibration particles in the collected waste stream 123 is an indication that the drop delay time is incorrect. As also disclosed below, the drop delay time is varied and data is collected for various drop delay times, so that a proper drop delay time can be selected.

Figure 2:
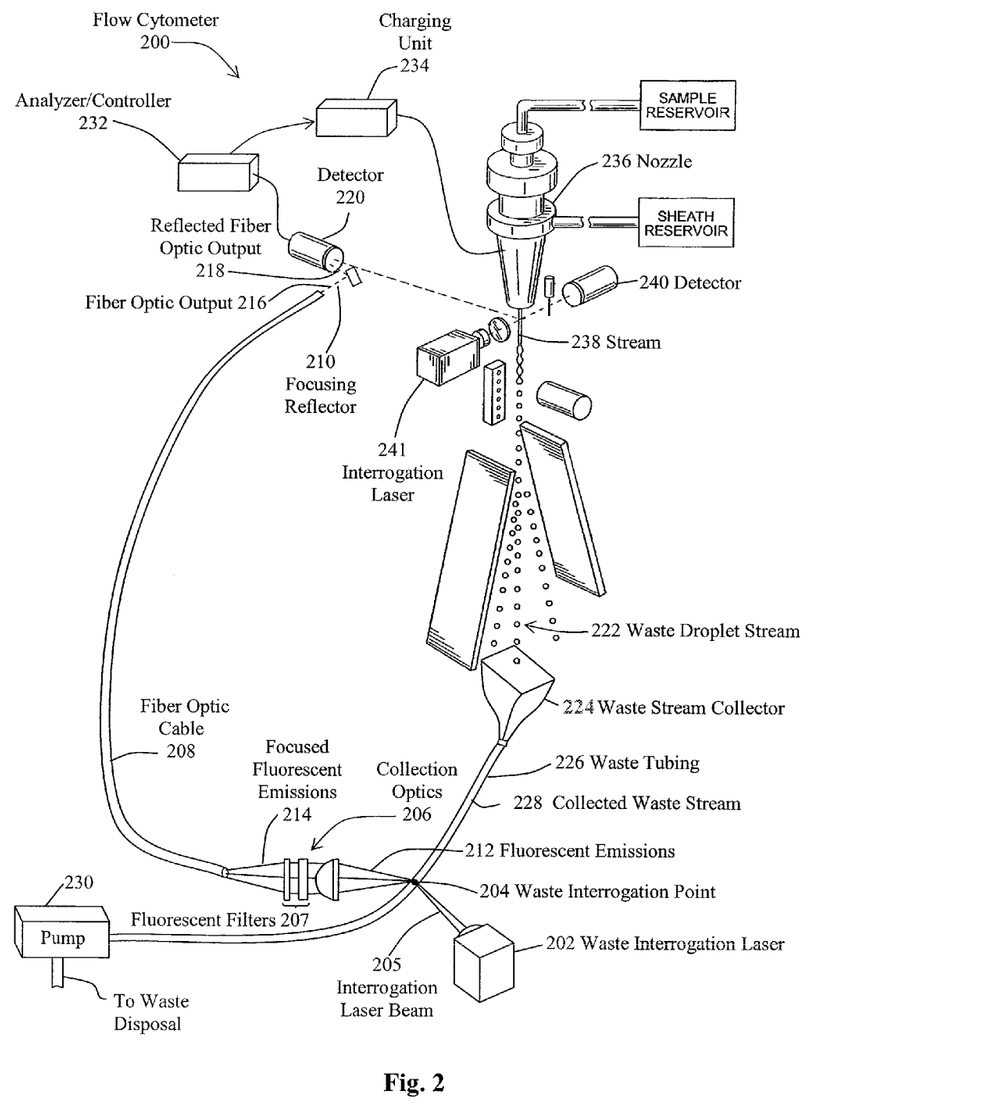
FIG. 2 is a schematic isometric view of another embodiment of the present invention.

FIG. 2 is a schematic isometric view of another embodiment of a flow cytometer 200. As illustrated in FIG. 2, the waste droplet stream 222 is collected in the waste stream collector 224 in a manner similar to that shown in FIG. 1. Waste tubing 226 transports the collected waste stream 228 via pump 230. The waste interrogation laser generates a laser beam that interrogates the collected waste stream 228 at the waste interrogation point 204. Fluorescent emissions 212 are generated by calibration particles that have been tagged with a fluorescent marker or calibration beads that have fluorescent properties. The collection optics 206 collects the fluorescent emissions 212 and generates a focused fluorescent emission 214 that is applied to the input of a fiber optic cable 208. En route to fiber optic cable 208, the focused fluorescent emissions 212 are filtered by the fluorescent filters 207, such that the focused fluorescent emissions 214 do not substantially include the scattered light from laser beam 205. The fiber optic cable 208 transmits the focused fluorescent emissions 214 to the output of the fiber optic cable 208. The fiber optic output 216, which comprises the focused fluorescent emissions 214, are directed to a focusing reflector 210. The focusing reflector 210 generates a reflected fiber optic output 218 that is applied to the input of detector 220. Detector 220 is used to detect both the fluorescent emissions 212 from the collected waste stream 228 and fluorescent emissions from particles in the stream 238. The output of the detector 220 is applied to an analyzer/controller 232 that separates data from the detector 220, as explained in more detail below. The analyzer/controller 232 is coupled to a charging unit 234 to charge the nozzle 236 in the same manner as described above with respect to FIG. 1.

During the process of calibrating the flow cytometer 100 for sorting particles based upon drop delay time, calibration beads are typically utilized that are provided in a steady stream from the sample reservoir 104. As indicated above, the calibration beads may be constructed, at least in part, by a fluorescent material that provides consistent and strong fluorescent emissions. Of course, other ways and other types of particles can be used for calibration purposes, including particles that create a scattered emission that can be detected by a detector such as detector 134. In addition, other techniques can be used comprising but not limited to visible camera based detection and impedance methods, such as the Counter Principle.

Since the calibration particles from the sample reservoir 104 are supplied at a substantially constant flow rate, the calibration particles in the collected waste stream 123 flow through the waste tubing 126 at a substantially constant rate. As explained in more detail below, the substantially constant rate of flow of calibration particles in the collected waste stream 123 allows for an accurate method of determining the number of calibration particles in the waste stream for each drop delay period.

The embodiment of FIG. 2 uses only a single detector 220 to detect both fluorescent emissions from stream 238 and fluorescent emissions 212 from the collected waste stream 228. Since the photomultiplier tube detectors can be expensive, the cost of the overall flow cytometer 200 can be reduced by utilizing the single detector 220 for detecting both the fluorescent emission of particles from the stream 238 (primary event) and the fluorescent emissions 212 from the collected waste stream 228.

The calibration particles in the collected waste stream 228 have a velocity that is substantially less than the velocity of the calibration particles in stream 238. For example, calibration particles in stream 238 may move at a velocity of approximately 20 m/s based on driving pressure of 30 PSI and a nozzle exit orifice of 100 μm. On the other hand, calibration particles in the collected waste stream 228 move at a velocity of only approximately 1.25 m/s due to the 500 μm internal diameter of the waste tubing 126 which is much larger than the nozzle exit orifice. In this example the calibration particles in the stream 238 may be moving at 16 times the velocity of those in the waste stream 228. The fluorescent emissions 212 are generated while the calibration particle is interrogated by the waste interrogation laser 202 at the waste interrogation point 204. After the calibration particles move through the interrogation laser beam 205, the fluorescent emissions cease. Of course, the same is true for calibration particles that are interrogated by interrogation laser 241 in stream 238. The difference is that the calibration particles in stream 238 pass through the laser beam from interrogation laser 241 at a much higher speed and, as such, create a much narrower time pulse that is detected by detectors 220, 240, than the broader pulse that is generated by the detector 220 as waste particles pass through the waste interrogation point 204 at a much slower speed (e.g. 16 times less). Some prior art methods attempt to use high speed, expensive cameras to detect the presence of calibration particles in deflected droplet streams, such as deflected droplet streams 118, 120. Because of the high speed at which the droplets are moving, high speed, expensive cameras are required to detect calibration particles in the deflected droplet streams 118, 120 and may produce incorrect results if the emissions are missed because of the short duration of the pulses that are produced.

Because of the differences in the pulse width, the output at detector 220 can easily distinguish between pulses generated by calibration particles in the collected waste stream 228 and pulses generated by calibration particles in stream 238. For example, and not by way of exclusion, electronic exclusion techniques can be used by simply comparing the outputs of detector 220 and detector 240 to exclude the narrower pulses generated by calibration particles in stream 238. As another example, electronic filtering can be used to separate the narrower pulses from the broader pulses. Further, the broader pulses, generated by the calibration particles in the collected waste stream 228, can be distinguished from noise by determining if the pulse has a sufficient magnitude for a sufficient amount of time to qualify as an emission from a calibration particle. For example, the analyzer/controller 232 may analyze the pulse to determine if the pulse has a magnitude greater than a predetermined threshold for a predetermined period, as explained in more detail with respect to FIG. 7.

Figure 3:
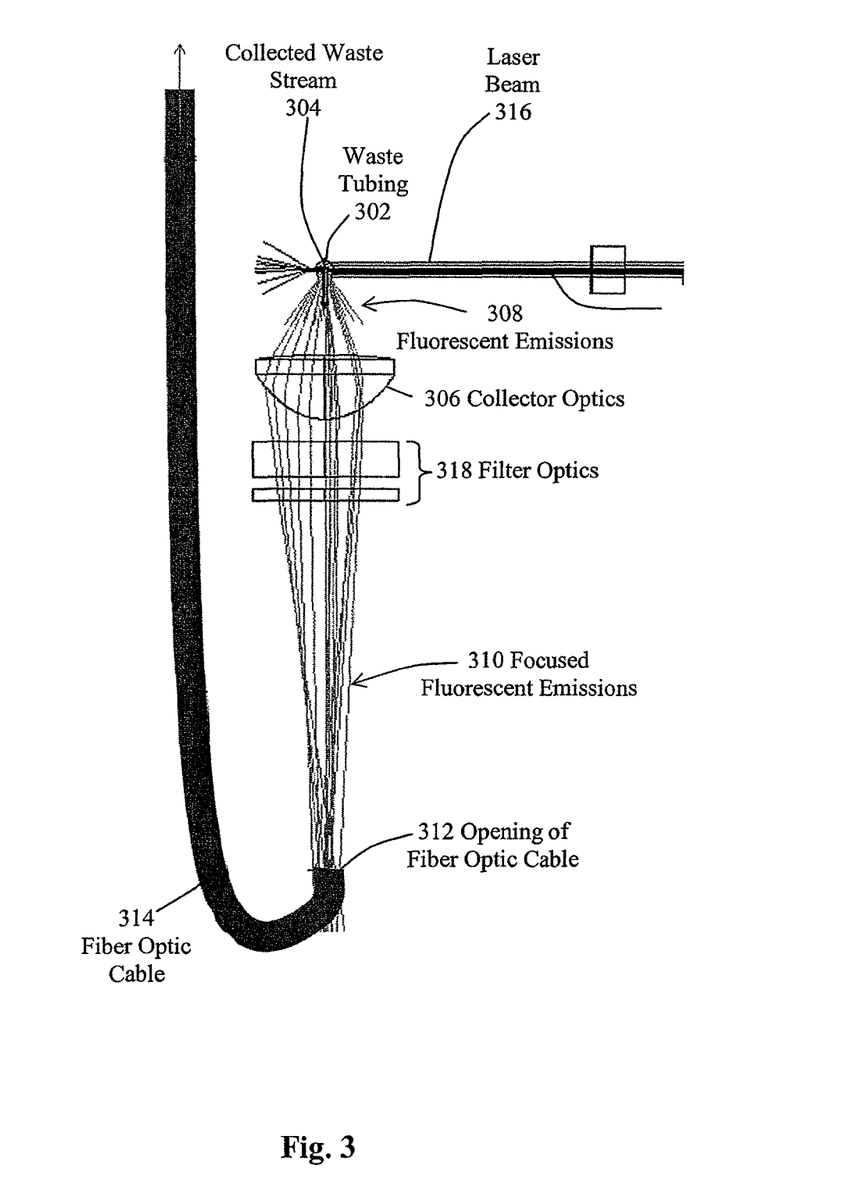
FIG. 3 is a schematic side view of the collector optics and a fiber optic cable for collecting scattered light.

FIG. 3 is a schematic side view illustrating an embodiment in which fluorescent emissions 308 can be collected, filtered and focused into a fiber optic cable 314. As shown in FIG. 3, collector optics 306 are disposed in a location to receive the fluorescent emissions 308 from the waste tubing 302 that are generated by particles that are interrogated by laser beam 316. As explained above, the collected waste stream 304 in waste tubing 302 is interrogated by an interrogation laser beam 316, so that fluorescent emissions 308 are generated by calibration particles. The collector optics 306 collects and focuses the fluorescent emissions 308 to generate focused fluorescent emissions 310. During transit, the fluorescent emissions are filtered by the filter optics 318 so that substantially only fluorescent light is included in the focused fluorescent emissions. The filtered, focused fluorescent emissions 310 are focused on the opening 312 of the fiber optic cable 314. Fiber optic cable 314 then transmits the focused fluorescent emissions 310 to a focusing reflector 406, as illustrated in FIG. 4.

Figure 4:
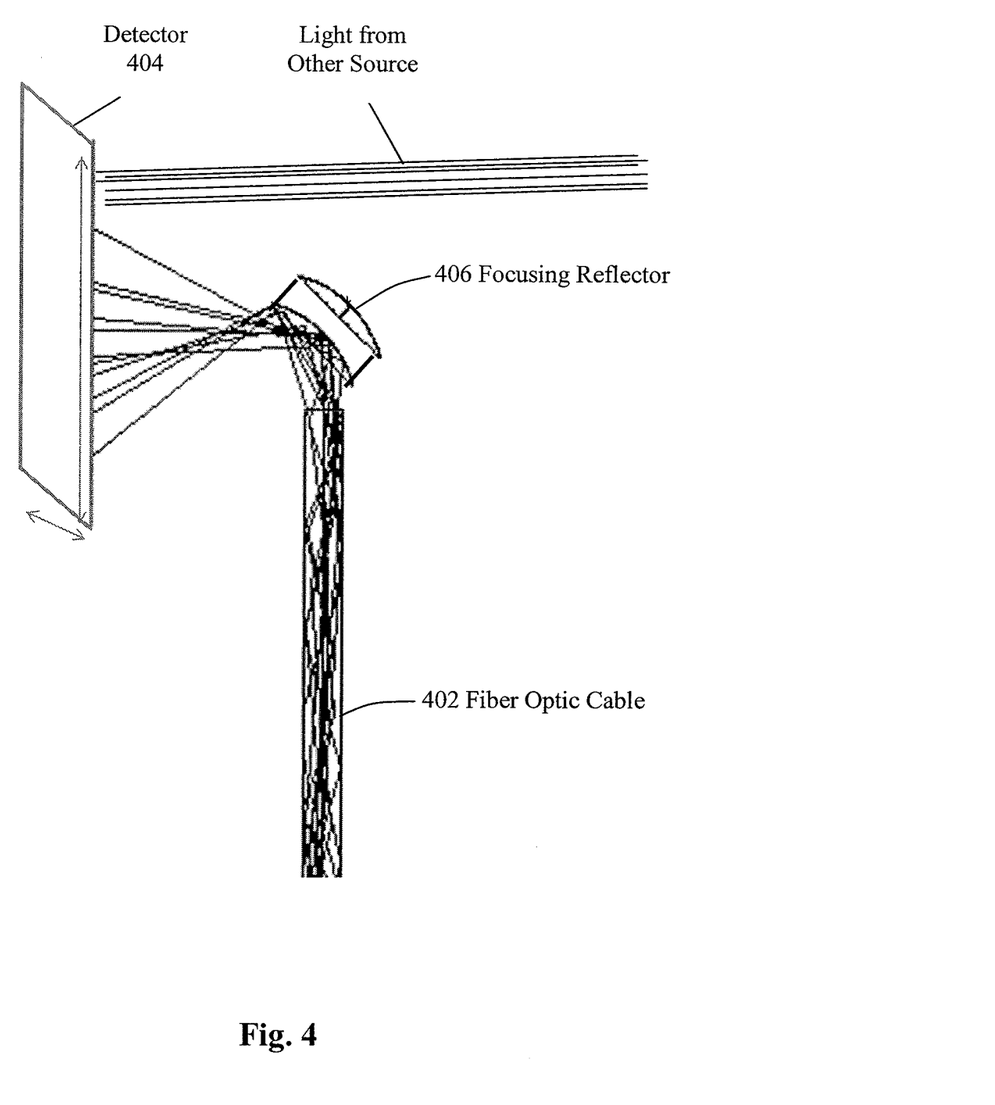
FIG. 4 is a schematic isometric view of the reflector optics that transmit the fluorescent emissions on a detector.

FIG. 4 is a schematic isometric view illustrating an embodiment in which the fluorescent emissions from the fiber optic cable 402 can be focused by the focusing reflector 406 on a detector 404. As shown in FIG. 4, the fluorescent emissions are transmitted by the fiber optic cable 402 to a location proximate to the focusing reflector 406. The laser emissions exiting the fiber optic cable 402 are focused by the focusing reflector 406 to a detector 404. The projection of light from focusing reflector 406 onto a plane, as illustrated in FIG. 3, matches the optical detection area of the photomultiplier tube detector 404. In this manner, the detector can produce a reliable and consistent output from the fluorescent emissions of waste calibration particles in the waste stream. Collected light, which constitutes fluorescent emissions from the interrogation point of primary stream 238, is shown as also impinging on detector 404.

Figure 5:
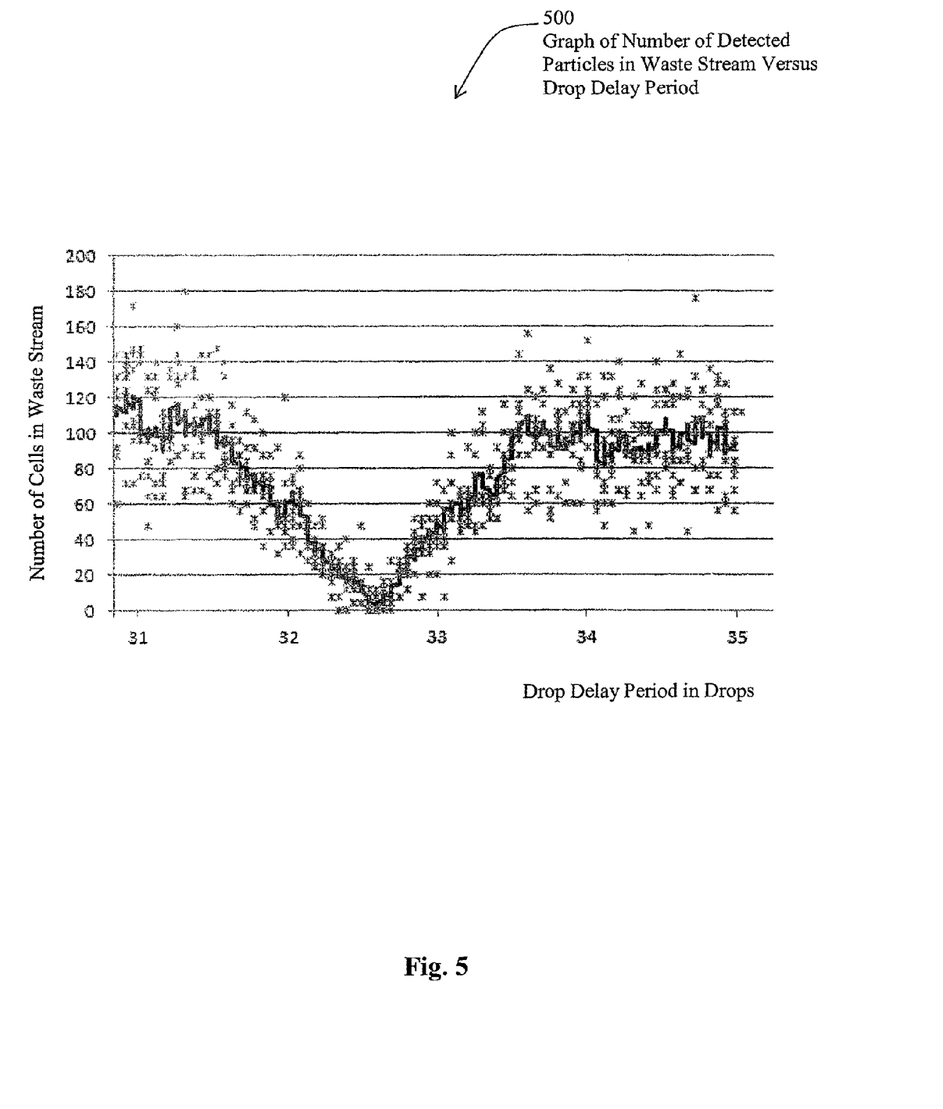
FIG. 5 is a graph of the number of detected calibration particles in a waste stream versus drop delay.

FIG. 5 is a graph 500 illustrating the number of detected calibration particles in the waste stream versus the drop delay period. FIG. 5 illustrates the various data points, as well as a smoothing curve, which is a simple average of the various data points. As shown in FIG. 5, data is collected multiple times for each drop delay period. For example, FIG. 5 illustrates five different calibration particles counts (waste particle detection periods) for each drop delay period, which are shown as small Xs in FIG. 5, that are averaged to create the darker curve, illustrated in FIG. 5. For example, for each drop delay period of FIG. 5, there are five samples that are taken. Each of the Xs that are vertically aligned for that drop delay period indicate the number of calibration particles that were detected over a predetermined sampling period. For example, a sampling period (waste particle detection period)

may comprise 250 milliseconds, during which a detector detects the number of particles in the waste stream. This process is repeated five different times for each drop delay period, in the example illustrated in FIG. 5, to determine the number of calibration particles in each of the five different 250 millisecond periods (waste particle detection periods). In this manner, multiple data points can be collected and averaged to provide more accurate data. Of course, a fewer or larger number of waste particle detection periods can be used for each drop delay period depending upon the desired speed and accuracy of the calibration process. The averaging of the data, as shown by the solid line in FIG. 5, clearly indicates the minimal point in the curve, which is 32.59 drops. The minimal point is the drop delay period that results in the fewest number of calibration particles in the waste stream and indicates the optimal drop delay period. Of course, other techniques can be used, other than just detecting the minimum value of an average signal, including using derivatives to determine curve slopes, curve fitting, cluster analysis and other techniques. One example of a method of determining the optimal drop delay period, is to use a two pass system, where the goal of the first pass is to ascertain an approximate value for the drop delay. Once the approximate value of the drop delay is determined, a finer sweep can be performed to hone in on the precise value. The coarse drop delay operates by sweeping a range of potential drop delays determined by the drop delay frequency, amplitude and sheath pressure. The number of calibration particles in the waste stream is sampled five times per second, for a total of one second, for incrementing the drop delay by the configured coarse step size, which is typically one-half drop. The five readings at each drop delay period are averaged (mean) and the drop delay in the lowest mean is used to perform the fine sweep. The fine sweep is centered on the coarse drop delay, ranging from minus one-half drop to plus one-half drop, i.e., the coarse drop delay increment. The fine sweep increment can be tailored to the desired precision, but is typically set to 0.05 drops. Once again, the waste particle detection period is repeated five times for each drop delay period and the readings are averaged. The ideal drop delay is then determined by smoothing the curve and picking the global minimum.

Figure 6:
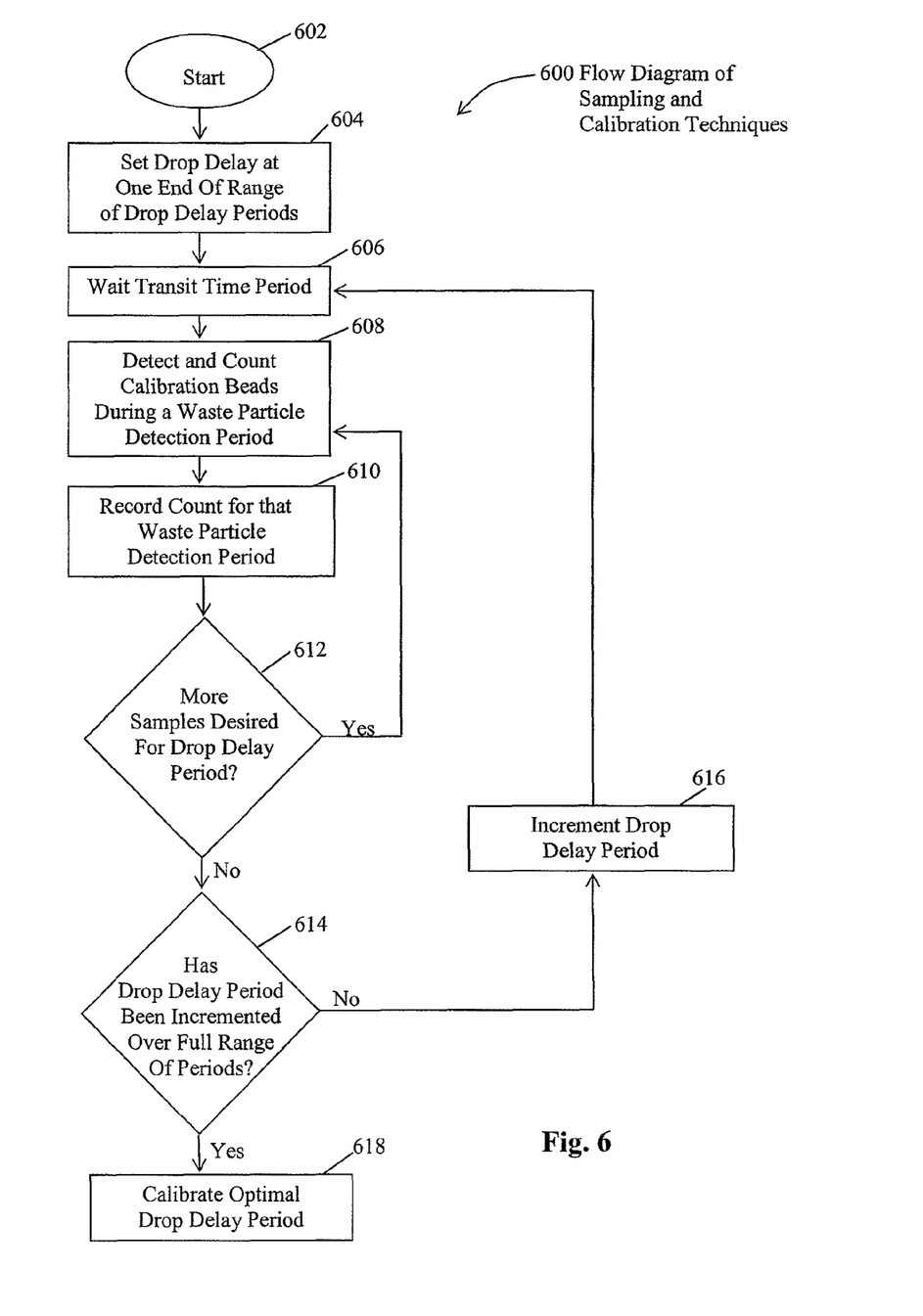
FIG. 6 is a flow diagram of one embodiment disclosing sampling and calibration techniques.

FIG. 6 is a flow diagram 600 of the sampling and calibration techniques used in accordance with one embodiment of the present invention. As illustrated in FIG. 6, the process starts at step 602. The flow cytometer 100 is loaded with calibration particles in the sample reservoir 104. The calibration particles flow through the nozzle 102 at a substantially constant rate and are surrounded by a sheath fluid. At step 604, the drop delay is set at one end of the range of suitable drop delay periods. The system then waits a length of time, referred to as the transit time, which is the time that it takes for a calibration particle to travel from the interrogation point 113 to the waste interrogation point 144. By waiting a time period that is equal to the transit time, or a time period that is slightly greater than the transit time period, from the start of each drop delay period, it is assured that particles for that drop delay period are being detected at the waste interrogation point 144, assuming that the waste particle detection period is less than the drop delay period. The waste particle detection period is the period of time during which particles are detected at the waste interrogation point 144. There may be multiple waste particle detection periods for each drop delay period so that multiple data points can be collected for each drop delay period. The drop delay period is the period of time during which a selected drop delay is utilized by the flow cytometer 100 to generate data for that selected drop delay.

At step 608 of FIG. 6, the calibration particles are detected and counted during a waste particle detection period. The particle count is then recorded for that waste particle detection period at step 710. The waste particle detection period for the data illustrated in FIG. 5 is 0.25 seconds. The same drop delay is maintained for the entire drop delay period, which includes multiple waste particle detection periods. The process then proceeds to step 612, where it is determined whether more samples are desired for the current drop delay period. If it is determined that more samples are desired for the drop delay period, the process returns to step 608 and another waste particle detection period is started. The calibration particles are then detected during the next waste particle detection period, at step 608, and the number of detected calibration particles are recorded at step 610. The process then proceeds again to step 612, to determine if more samples are desired. In the data illustrated in FIG. 5, five samples (i.e., five waste particle detection periods) were recorded for each drop delay period. If it is determined at step 612 that additional samples are not desired, the process proceeds to step 614 to determine if all of the drop delay periods have been incremented over the full range of drop delay periods. For example, in the data illustrated in FIG. 5, there are multiple drop delay periods, i.e., on the order of eighty drop delay periods, as indicated along the axis of FIG. 5. If all of the drop delay periods have not been incremented, the process proceeds to step 616, where the drop delay period is incremented. The process then returns to step 606, so that new data can be recorded for the next drop delay period. At that point, a new drop delay period is initiated. If the drop delay period has been incremented over the full range of periods, at step 614, the process proceeds to step 618, where the flow cytometer 100 is calibrated to operate at the optimal drop delay period.

Figure 7:
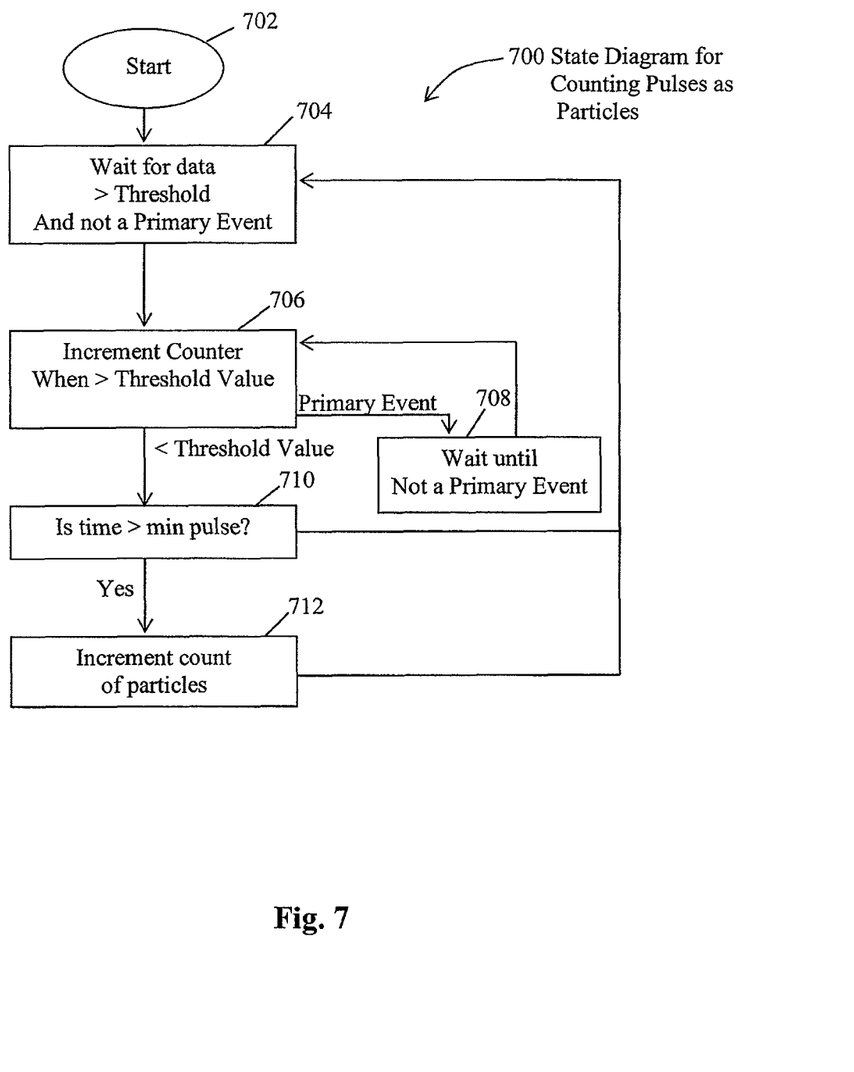
FIG. 7 is a state diagram of one embodiment for counting pulses as particles.

FIG. 7 is a state diagram 700 illustrating the process for counting pulses as particles in accordance with the detection of particles at the waste interrogation point 144 and to distinguish calibration particles from noise. The process starts at step 702. Detector 134 generates an electronic signal from the fluorescent emissions 132 and transmits that signal to the controller/analyzer 140. At step 704, the controller/analyzer 140 waits for data that is greater than a threshold value and which is not a primary event. A primary event is a detection by detector 220 of calibration particles in stream 238 of the embodiment of FIG. 2. In the embodiment of FIG. 1, a separate detector 134 detects the fluorescent emissions 132, so that an exclusion of a primary event is not needed. At step 706, a counter is incremented when the magnitude of the fluorescent emission is above a threshold value. In accordance with the embodiment of FIG. 2, if a primary event occurs, the counting is paused at step 708 and the system waits until the primary event has finished. Once the magnitude of the fluorescent emission drops below the threshold value, a comparator is used to compare the count in the counter with the count for a minimal pulse. If it is less than the number of counts for a minimal pulse, the process returns to step 704. If it is greater than the number of counts for a minimal pulse, the process proceeds to step 712 and a separate counter, that counts the number of pulses, is incremented to indicate the number of particles. The process then returns to step 704.

Accordingly, the embodiments of the present invention provide an accurate way of automatically calibrating the drop delay by counting the selected particles in the waste stream. The drop delay is incremented over a number of different drop delays and the system determines the drop delay for which the least number of calibration particles are present in the collected waste stream 123. The system analyzes this data and selects the drop delay period having the minimal number of calibration particles. In addition, a single detector 220, in the embodiment of FIG. 2, can be used to count primary events, as well as waste stream events, to further reduce cost, by using a single detector 220 to perform both operations.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A flow cytometry system for selecting a desired drop delay for a flow cytometer, the flow cytometer comprising:
    means for forming a stream such that the stream forms droplets at a droplet separation point;
    means for interrogating the stream at an interrogation point upstream of the droplet separation point, wherein the desired drop delay is representative of the elapsed time between when particles pass through the interrogation point and when a droplet containing the particles separates from the stream at the droplet separation point;
    means for charging the droplets;
    means for electrostatically deflecting the droplets;
    waste tubing configured to form a waste stream that is generated from droplets that are not deflected by the means for electrostatically deflecting the droplets;
    a waste stream optical source configured to illuminate the waste stream in the waste tubing;
    a detector configured to sense scattered light or fluorescent emissions from calibration particles in the waste stream; and
    a controller that is configured to:
        operate the flow cytometer for a plurality of drop delay periods while calibration particles are present in the stream, each drop delay period having a different selected drop delay from a range of potential selected drop delays,
        cause the means for charging to charge the droplets during each drop delay period according to the selected drop delay for that drop delay period,
        cause the means for electrostatically deflecting the droplets to deflect the charged droplets during each of the drop delay periods,
        determine information indicative of a rate at which the calibration particles enter the waste stream during each drop delay period based on the sensed scattered light or fluorescent emissions from the calibration particles in the waste stream, and
        determine the desired drop delay based upon the information indicative of the rate at which the calibration particles enter the waste stream during each drop delay period.

2. The system of claim 1, wherein the controller is further configured to set the selected drop delay of the flow cytometer to the desired drop delay.

3. The system of claim 1, further comprising a pump configured to draw the waste stream through the waste tubing at a flow rate greater than a flow rate at which the stream is flowed.

4. The system of claim 1, wherein the waste tubing has a larger internal diameter than an exit orifice diameter of a nozzle of the means for forming the stream.

5. The system of claim 1, wherein the controller determines the desired drop delay using pattern recognition techniques.

6. The system of claim 1, wherein the detector is also used to detect the calibration particles at the interrogation point in the stream.

7. The system of claim 6, further comprising:
    one or more optical collectors aligned to collect said the scattered light or fluorescent emissions from the calibration particles in the waste stream; and
    one or more fiber optic cables aligned to transmit the scattered light or fluorescent emissions to the detector.

8. The system of claim 1, further comprising:
    a display that visually displays the amount of calibration particles in the waste stream for the each drop delay period to allow an operator of the flow cytometer to select a drop delay period.

* * * * *